US009642770B2

(12) United States Patent
Storch

(10) Patent No.: US 9,642,770 B2
(45) Date of Patent: *May 9, 2017

(54) RABBUTT-DILDO GEAR FOR LESBIANS, PEGGING AND MASTURBATION

(71) Applicant: Leonard Storch, New York, NY (US)

(72) Inventor: Leonard Storch, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/366,000

(22) Filed: Dec. 1, 2016

(65) Prior Publication Data

US 2017/0079874 A1 Mar. 23, 2017

Related U.S. Application Data

(63) Continuation-in-part of application No. 15/001,317, filed on Jan. 20, 2016, now Pat. No. 9,510,995.

(60) Provisional application No. 62/107,721, filed on Jan. 26, 2015.

(51) Int. Cl.

| | |
|---|---|
| ***A61F 5/00*** | (2006.01) |
| ***A61H 19/00*** | (2006.01) |
| ***A41D 1/06*** | (2006.01) |
| ***A41D 1/02*** | (2006.01) |
| ***A41D 27/00*** | (2006.01) |
| ***A41D 1/14*** | (2006.01) |
| ***A41D 1/08*** | (2006.01) |

(52) U.S. Cl.

CPC ............... *A61H 19/44* (2013.01); *A41D 1/02* (2013.01); *A41D 1/065* (2013.01); *A41D 1/08* (2013.01); *A41D 1/14* (2013.01); *A41D 27/00* (2013.01); *A61H 19/34* (2013.01)

(58) Field of Classification Search

CPC ........ A61H 19/00; A61H 19/30; A61H 19/34; A61H 19/40; A61H 19/44; A61H 19/50; A41D 1/06; A41D 1/065

USPC ............................ 600/38–41; 2/79, 234, 408

See application file for complete search history.

(56) References Cited

U.S. PATENT DOCUMENTS

| | | | |
|---|---|---|---|
| 4,578,828 | A | 4/1986 | Smith, Sr. et al. |
| 5,690,603 | A | 11/1997 | Kain |
| 5,725,473 | A | 3/1998 | Taylor |
| 6,203,491 | B1 | 3/2001 | Uribe |
| 6,418,931 | B1 | 7/2002 | Bloodsaw |

(Continued)

OTHER PUBLICATIONS 4 pages from copending application PCT/US16/014693 dated Jun. 20, 2016: Amazon.com Strp U Dual Pleasure Strap on.

(Continued)

*Primary Examiner* — John Lacyk

(57) ABSTRACT

Sex paraphernalia comprising a platform assembly 7 (Rabbutt™) which has a dildo 11 on one side facing one way and a rabbit 13 on the other side facing the other way, configured so that, when Pants with a crotch opening (Rabbutt Hole Pants™) as disclosed herein, or a strap-on dildo harness, are worn by a lady user with the rabbit side of the assembly inside facing her clitoris and the dildo sticking out through the opening, she may insert the dildo into a partner with the rabbit pleasing her clitoris while she bangs away. Pants may have cutouts for spanking or caressing. Pants may be suitable for outdoor wearing (without the platform assemble) to attract a sex partner who is in-the-know, or to raise questions from others like, what's the hole for? Jackets suitable with Pants may complete the ensemble. Embodiments also lend themselves to a lone lady for masturbation.

6 Claims, 10 Drawing Sheets

(56) References Cited

U.S. PATENT DOCUMENTS

| | | | |
|---|---|---|---|
| 6,890,293 | B2 | 5/2005 | Kobayashi |
| 7,513,868 | B1 | 4/2009 | Fontenot |
| 8,308,667 | B2 | 11/2012 | Lee |
| 8,500,627 | B2 | 8/2013 | Lee |
| 8,657,766 | B2 | 2/2014 | Tuck et al. |
| 8,672,832 | B2 | 3/2014 | Lee |
| 8,721,523 | B2 | 5/2014 | Lee |
| 8,747,337 | B2 | 6/2014 | Lee |
| 8,876,695 | B2 | 11/2014 | Wilson et al. |
| 8,915,835 | B2 | 12/2014 | Lee |
| 9,005,110 | B2 | 4/2015 | Lee |
| 9,114,058 | B2 | 8/2015 | Lee |
| 9,510,995 | B1 * | 12/2016 | Storch .................... A61H 19/44 |
| 2004/0199046 | A1 | 10/2004 | Astin |
| 2008/0119767 | A1 | 5/2008 | Berry |

OTHER PUBLICATIONS

Two (2 pages) Internet webpages for sex toys downloaded on Dec. 30, 2015 from “Lovehoney Ltd”:“Fetish Fantasy Elite 7 Inch Penetrix Double Dildo Vibrator.”.

* cited by examiner

RABBUTT-DILDO GEAR FOR LESBIANS, PEGGING AND MASTURBATION

This application claims priority to Ser. No. 15/001,317 confirmation number 1087 filed on Jan. 20, 2016 which is scheduled to issue on Dec. 6, 2016 as U.S. Pat. No. 9,510,995; and, this application claims priority to Provisional Ser. 62/107,721 confirmation number 9764 filed Jan. 26, 2015. The entire contents of these two applications are hereby incorporated herein by reference thereto.

FIELD OF ART

The field of art embraces sex play paraphernalia. Among items commercially available in the prior art for sex play are rabbits for clitorises and dildos for vaginas, anuses, mouths and hands. Rabbits and dildos come with or without vibrators to increase sexual pleasure as can the novel paraphernalia disclosed herein come. Such items and others are made of a variety of safe-for-human-insertion materials including, for example, silicone, rubber, plastic, wood, metal, porcelain, ceramic, pottery. Also among items commercially available in the prior art for sex play are strap-on dildo harnesses and undergarments with an opening to accommodate a dildo for sex play.

Societal-wise, the Field of Art has become less "taboo." Perhaps our USSC's 2015 marriage ruling was a societal milestone regarding prudish 1950's sexual bigotries which include, for example, talking about or showing sexual matters in public. Indeed, on Jan. 1, 2016, the New York Times published this article by Elaine Sciolino: "*Lifting the Veil on the New York Public Library's Erotica Collection.*"

On Jan. 9, 2016, an article titled, "*Orgasmic design: how vibrators have become ambitious tech products*"—"*The vibrator's long, slow march from taboo to mainstream* (*and maybe even cool*) *has been all about figuring out what exactly women want*" was published on a few Internet webpages. Reportedly, Barbara Walters even gave her personal vibrator a pet name, "Selfie."

DEFINITIONS

Dildo: A "dildo," as discussed herein, is sexual apparatus, something generally shaped like an erect penis, to be inserted into a body's opening for sexual pleasure. A dildo may be called a faux penis or a phallic device. Dildos come in great variety; for example, some available dildos that ejaculate are called ejaculating dildos or squirting dildos.

Rabbit: Rabbits, or bunnies, are known to be sexually prolific. A bunny, or rabbit, is the logo for Hugh Hefner's Playboy products. For purposes herein, however, a "rabbit head" or just "rabbit" means sexual apparatus, something that is designed to give a woman sexual pleasure by contacting and/or massaging her clitoris.

The clitoris (clit) is complex; its size and sensitivity vary. The glans (head) of the human clitoris is roughly the size and shape of a pea, and its thousands of nerve endings make it the most sensitive erogenous zone. The clitoral hood is a fold of skin that covers at least part of the head and external shaft of the clitoris for protection; the use of a rabbit allows stimulation more directly on the clitoris.

Different "rabbit heads" or "rabbits" (rabbits 169 to 179*c*) are depicted in FIG. 12. Rabbit head or rabbit as used herein does not mean a "jack rabbit sex toy" (which is described below). A woman may derive sexual pleasure in various ways when a rabbit is in contact with her clitoris. Enjoyable and satisfying clitoral "massage" pleasure may be achieved, for example, by wiggling, writhing, thrashing about or rubbing a clitoris against a rabbit or a rabbit against a clitoris; and, a rabbit just touching or being in contact with a clitoris can be arousing. A rabbit may or may not be associated with a vibrator (well known in the sex paraphernalia art). A rabbit may or may not also be associated with a dildo (a "jack rabbit" example is described below).

Platform assembly: Sex paraphernalia of the present inventions include a "platform assembly" which is disclosed and pictured herein. A "platform assembly" is generally shaped like an elongated irregular oval as depicted in FIG. 7. It may also be shaped like an elongated oval or an egg shaped oval; the shape of a platform assembly need not be regular; for example, the shape of the top portion may differ from the shape of the bottom. In one embodiment, a platform assembly has a dildo on one side and rabbit on the other side facing away from the dildo. A platform assembly, with for example, a dildo and rabbit, may be fabricated like other sex toy dildos, such as being a single molded piece of, for example, silicone, or the rabbit and dildo may be detachably mounted. A platform assembly may, for example, be flexible and soft for functional and comfort purposes, or a platform assembly may be somewhat rigid, for example, to facilitate masturbation embodiments. As described below, a platform assembly's stiffness can also vary; for example, between the upper, mid and lower areas (parts of the assembly).

Applicant is not aware of any prior art similar to a "platform assembly" with a rabbit facing one way and a dildo facing the other way. A platform assembly is configured for a couple to enjoy as follows: to be worn in new and useful "pants with a crotch opening" or just "pants" as disclosed and pictured herein or used in a commercially available strap-on dildo harness, so that a lady can pleasure herself with the rabbit side of the platform assembly inside facing her clitoris, while the dildo on the other side of the assembly sticks out thru the opening so that the lady may insert it into a female or a male partner to also give her or him sexual pleasure. A platform assembly may be used by one lady for masturbation with or without pants or a harness, as described below.

Pants: Sex paraphernalia of the present inventions includes "pants with a crotch opening" (the opening not to be confused with a "fly") or "hole pants" or just "pants" or "Pants" as disclosed and pictured herein to be worn with or without a platform assembly. Pants may be worn indoors or out with or without underpants (undergarments). Pants, which includes skirts-with-a-crotch-opening and suitable jackets, refers to outerwear type of clothing which is suitable for wearing outdoors as opposed to underwear which is unsuitable for outdoor wearing (unless worn under outdoor clothing). Pants can hold a platform assembly or a commercially available dildo; one advantage of pants is that pants hold such sex paraphernalia more firmly in place (which is a particular advantage during, for example, sexual intercourse, which is referred to herein as "banging") as opposed to, for example, commercially available strap-on harnesses. Also, generally, pants are more attractive than commercially available harnesses. Pants may be made of any kind of cloth comprising wool, cotton, denim, silk, canvas, other fabrics etc., and other materials, leather, faux leather, latex, rubber etc. Pants may be made available with a jacket suitable to wear with the Pants; for example, pant suits, with a crotch hole in the Pants. The jacket may or may not be long enough to cover the crotch hole when the jacket is buttoned.

Holder: A strap-on dildo harness, and "pants with a crotch opening" or "pants," may be referred to herein as a "holder" meaning pants or a strap on harness worn to hold a "platform assembly." A provider of platform assemblies or pants with a crotch hole may ask a potential customer about an anatomical measurement(s) of the intended user; for example, a measurement involving the location of her clitoris in reference to another part(s) of her anatomy, such as her pubic symphysis.

Taint: The perineum, meaning the area between the anus and the scrotum or the vagina.

Welt; Welt edge: The raised or strengthened edge part of a garment, which is around an opening, for reinforcement and/or ornamentation. The welt edge may be sewn in or onto a garment or otherwise made part of the garment. The welt edge delineates (indicates the position of the edge) a rounded, oval or other shaped opening.

Bang: Bang is considered more politically correct than the f-word it replaces. Chosen for versatile convenience, the meaning of "bang" as used herein is defined as follows. This meaning was found on a dictionary link for merriam-webster.com/dictionary/bang:

"transitive verb . . . 3 often vulgar: to have sexual intercourse with".

The choice of "bang", "banging", "bangs" and their derivations was convenient to refer to sexual activity including intercourse; for example, banger is used herein to refer to a banger giver who inserts the dildo into a bangee receiver of the dildo, the one being banged.

Pegging: The meaning of "pegging" as used herein is defined as follows. This meaning was found on this dictionary link: urbandictionary.com/define.php?term=pegging "pegging" means: "anal sex reversed. instead of the man sticking his penis up the womans butt, the woman wears a strap-on and sticks it up the mans butt."

This clever rather telling dialogue follows that definition on the pegging link by way of providing further information, explanation, clarification and example:

"charles: are you sure jean? you probably won't feel anything.

jean: i don't care charles. i'll do anything for you. (jean proceeds to peg charles, . . . "

SUMMARY, OBJECTS & BACKGROUND

Charles' comment to Jean, "you probably won't feel anything" alludes to what is missing in the prior art, and what's missing is an object of what the present inventions address by providing a rabbit so Jean will feel (more) pleasure while pegging Charles.

And if Jean were, for example, in a lesbian relationship with a girlfriend named Charlene, the present inventions provide a rabbit so Jean will feel (more) pleasure while banging Charlene with the dildo.

It is an object of the inventions to disclose sex paraphernalia comprising a platform assembly 7 which has a dildo 11 on one side facing one way and a rabbit 13 on the other side facing the other way as depicted, for example, in FIG. 1.

It is another object of the present inventions to disclose "pants" to hold a "platform assembly" with a dildo on one side facing one way and a rabbit on the other side facing the other way. The pants provide Jean more intimate feel and control of the dildo than does a strap-on harness; pants afford Jean a more realistic sensation of having a real penis.

It is another object of the present inventions to allow Jean more control of the dildo 11 and rabbit 13 on platform assembly 7 of FIG. 1, for example, while wearing platform assembly 7 in pants with rabbit 13 stimulating her clitoris for her pleasure while she bangs her partner with dildo 11.

It is an object of the inventions to disclose sex gear, sex paraphernalia, comprising outdoor wearable clothing comprising pants with a crotch opening available with or without a suitable jacket (which may or may not be long enough to cover the crotch opening), ostensibly to hold a platform assembly with a rabbit inside the pants and a dildo sticking out through the opening, the pants to be worn indoors or out by a lady with or without the assembly so that when worn with an assembly inside the pants the rabbit may pleasure her clitoris while she inserts the dildo, which is projected through the opening, into a partner, and when worn without the assembly the wearer may raise questions from those who know what the pants are for or questions from those who do not know what the pants are for. The clothing may comprise provision for the bangee to spank and/or directly caress the banger's exposed butt cheeks directly while being banged.

It is another object of the inventions to disclose sex gear for masturbation, i.e., single use: Embodiments of the invention can also be enjoyed by, for example, a lone lady while masturbating—while wearing the platform assembly in pants or in a strap on harness with the dildo portion sticking through the opening and the rabbit engaging her clitoris, the wearer can use the dildo to manipulate the rabbit to maximize the stimulation of her clitoris. Thus, a lady can pleasure her clitoris with a rabbit using a phallic device to control the sexual sensations. Embodiments of the invention can also be enjoyed in this manner without wearing the assembly in pants; e.g., a lady holds and controls the dildo with her hands while pleasing her clitoris with the rabbit. Also, if the dildo of the platform assembly were inserted somewhere (like into an inflatable doll, sex toy or improvised sex toy) or into an opening of a partner, a lady could avail herself of the pleasure from the rabbit without wearing pants. This single use masturbation pleasure sensation embodiment, as well as other embodiments, can be enhanced with vibrator technology well known in the sexual arts.

It is another object to disclose for the present dildo inventions (such as depicted for example in FIG. 1), the use of vibrators, ejaculating dildos, mechanized dildos and dildos textured with, e.g., blood vessels. Dildos come in great variety; for example, some available dildos that ejaculate are called ejaculating dildos or squirting dildos. For example, on Jan. 7, 2016, a dildo seller company, listed on the Internet as "gentletoys.com", listed 13 different "EJACULATING DILDOS" for sale. The first item listed, "DEEP DICKIN DEREK 12 INCH EJACULATING DILDO," was described as follows:

"Ready for some serious deep dickin? Get your hands on Derek and let the intense penetration begin! This formidable dildo is going to take you some patience and lube to accommodate its full length and girth, but experiencing the realistically detailed cock head and shaft slide in, all the way to the balls, will be an erotic reward all its own. Once you have conquered this behemoth, reward yourself with the ultimate payoff. Squeeze the balls and Derek will ejaculate on you or in you. The balls hold about half an ounce of liquid, and are easy to fill. Just place the tip in your liquid of choice, depress the balls, and release. Derek is fully loaded and ready to go!"

One of gentletoys.com's other ejaculating dildos, "VEINY VICTOR EJACULATING SQUIRT COCK WITH BOTTLE," comes "With a bellows style bottle for powerful squirting."

For example, mechanized dildo technology, such as patented by Inventor Lee, U.S. Pat. No. 9,114,058 issued on Aug. 25, 2015, may be incorporated with the present dildo inventions (such as depicted in FIG. 1).

It is another object of the inventions to disclose sex paraphernalia jewelry and art comprising charms, trinkets, pendants and sculptures. For example, charms, art and sculptures that look like a platform assembly shown, for example, in FIG. 1, may be made available as jewelry, art pieces, etc., and integrated in, for example, a sundial. For example, a Rabbutt used as the pointer in a sundial sculpture may be appropriate in front of the Playboy Mansion.

It is another object of the inventions described herein to have the potential to help herald in the notion of expanded sexual pleasures, and more intense sexual pleasures, to greater and greater numbers of people everywhere as they open their minds to embrace old and new notions about sex that had previously been taboo. Safely satiating sexual interests & drives (libido) is a good thing. For example, perhaps if war-mongers were more sexually satiated there would be less war, and this could have a "butterfly-effect." The mantra from the 1960s comes to mind, make love not war.

The BACKGROUND includes sex paraphernalia devices which are readily available with a dildo and a rabbit in which the dildo is pointed in the same direction as the rabbit, so that, for this general type of device, which may be referred to as a "jack rabbit" sex toy, the rabbit and dildo are directed to pleasure a lady's vagina and clitoris when the device is used. This prior art device is designed for one lady to use by inserting the dildo into her own vagina while massaging her clitoris with the rabbit. This general type of device is to be used in and on one lady at a time. Rabbit head or rabbit as used herein does not mean a jack rabbit sex toy. Googling "what is a rabbit for sex" produced an article titled: "Guide to Sex Toys. Rabbit vibrators—YouTube." Clicking on that article's link produced a video as well as this text that follows which describes a popular dildo/rabbit/vibrator combination product:

"Guide to Sex Toys. Rabbit vibrators

Uploaded on Jul. 17, 2011

Combination vibrators are currently very popular. They have the ability to stimulate the vagina like a traditional vibrator as well as stimulate the clitoris and/or the opening of the vagina at the same time. A good example of a combination vibrator is the Jack Rabbit. This is the most recognizable combination vibrator on the market because of its popularity and because it was featured on HBO's 'Sex and the City'. It consists of a small 'rabbit' perched on top of a pink jelly vibrator shaft. The rabbit is designed to directly stimulate the clitoris and is controlled by a remote battery pack. The shaft, which is also controlled by the remote battery pack, is capable of twisting back and forth and of 'rotating' the pearls around in a circular motion, which stimulates the labia and the opening to the vagina. Many women find the combined features of these vibrators to be the perfect recipe for orgasm. They require less work than other toys and the stimulation levels of the clitoral stimulator and the shaft can be adjusted independently to fit your mood. Combination vibrators are usually high quality toys and they come in many shapes and sizes. They're easy to use and work well for both experienced and novice vibrator users."

Googling "double dildo" and then clicking "images" produced a page of many images of different kinds of prior art dildos and people using them. For example, one image was of a "flying double dildo". I estimate the straight in-line "flying double dildo" shown to represent a sex toy about 14 inches long. It has a penis head at each end and two rabbit heads (shaped like little wings) sticking up from the middle, one facing in each direction corresponding to the direction of each penis head. I presume to help simulate real penises, replications of testicles are sticking down from the middle of the double dildo on the opposite side of the rabbit heads. Googling "flying double dildo" produced an article titled, "Osama Bin Laden Sex Toy Collection|Fleshone.com" which also shows the "flying double dildo." However, as of Dec. 30, 2015, I still couldn't find anything further about the "flying double dildo."

The prior art is replete with dildos facing opposite each other and dildos with rabbits facing the same way. Applicant is not aware of any prior art similar to a "platform assembly" (disclosed and pictured herein) with a rabbit facing one way and a dildo facing the other way that can be worn in new and useful "pants with a crotch opening" (disclosed and pictured herein) or used in a strap-on dildo harness, so that a lady can pleasure herself with the rabbit side of the platform assembly inside facing her clitoris, while the dildo on the other side of the assembly sticks out thru the opening so that the lady may insert it into another lady or a male partner to also give her or him pleasure. Neither is Applicant is aware of any "hole pants" prior art as disclosed and pictured herein.

I downloaded two Internet webpages for sex toys on Dec. 30 2015 from "LOVEHONEY LTD" which I found to be representative of various similar sex toys. I prepared those pages for filing with an IDS. I described them in the NON-PATENT LITERATURE DOCUMENTS box in the IDS as follows:

"Two Internet webpages for sex toys downloaded on Dec. 30 2015 from 'LOVEHONEY LTD': 'Fetish Fantasy Elite 7 Inch Penetrix Double Dildo Vibrator.' Link: http://www.lovehoney.com/product.cfm?p=22566#videos 'RodeoH Generation Strap On Harness Boxer Shorts with Vibe Pocket.' Link: http://www.lovehoney.com/product.cfm?p=28625

The bottom of these webpages have this notice:

Copyright © Lovehoney Ltd. Lovehoney® is a registered Trademark of Lovehoney Ltd. Registered Company 04637868. 100 Locksbrook Road, Bath, BA1 3EN, UK."

There are so many sex toys available from Internet websites that it boggles one's mind. The two sex toys, described as NON-PATENT LITERATURE DOCUMENTS in the IDS, appear to be most representative for purposes herein.

Dildos, rabbits, fashions and other elements of the figures depicted herein are not, of course, drawn to scale or proportion and their depiction in angles and clothing styles shown, etc., are not meant to be limiting.

DETAILED DESCRIPTION

Figure 1:
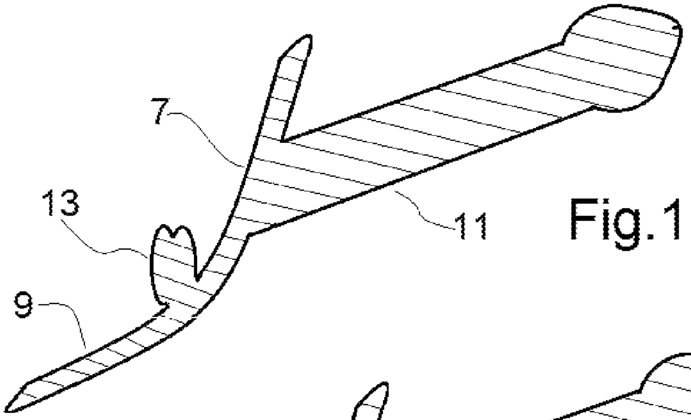
FIG. 1 is a side view of a platform assembly with dildo & rabbit.

The embodiment shown in FIG. 1 is a side view of a platform assembly with dildo 11 & rabbit 13. The lower portion 9 of platform assembly 7 is designed to extend below a lady user's clitoris while holding the rabbit 13 in contact with her clitoris. The lower portion 9 of platform assembly 7 as illustrated by way of example extends further, past her clitoris toward her taint to cover (envelop or veil) at least part of her vagina, or past her vagina to cover at least part of her taint. The lower portion 9 of platform assembly 7 may allow a more intimate feel and control of the dildo, especially if worn in pants; the lower portion 9 may afford a more realistic sensation of having a real penis while banging. The angle of dildo 11 relative to the platform assembly 7 may vary in accord with various embodiments of the present inventions; FIG. 1 depicts an angle about mid-way between a right angle (0° to 90°). However, for example, platform assembly 7 may be offered to users with dildos 11 at any angle relative to the platform assembly 7 that the user may want for a her and/or her bangee's banging desire, for example, for comfort, feeling, health reason(s), etc.

Figure 1A:
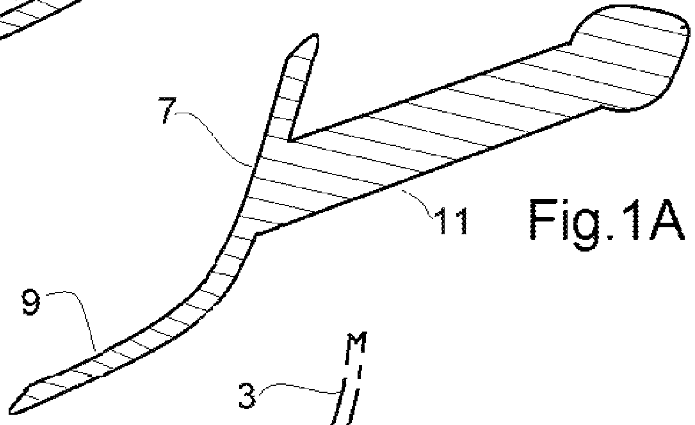
FIG. 1A is a side view of a platform assembly with a dildo.

FIG. 1A, another embodiment of the invention, is a side view of a platform assembly 7 with a dildo 11, no rabbit. The embodiment shown in FIG. 1A is for a female or male to wear in pants as described herein or in a strap-on harness. The lower portion 9, as described for FIG. 1, of the platform assembly 7 allows the user more intimate feel and control of the dildo. For comfort, a platform assembly 7 for a male may have a cutout opening (not shown) next to the area of his testicles (scrotum, balls) so that it does not press his testicles, and a hollow dildo is provided in the platform assembly 7 of FIG. 1A, so he may put his penis into it and use dildo 11 to bang his partner with.

Figure 2:
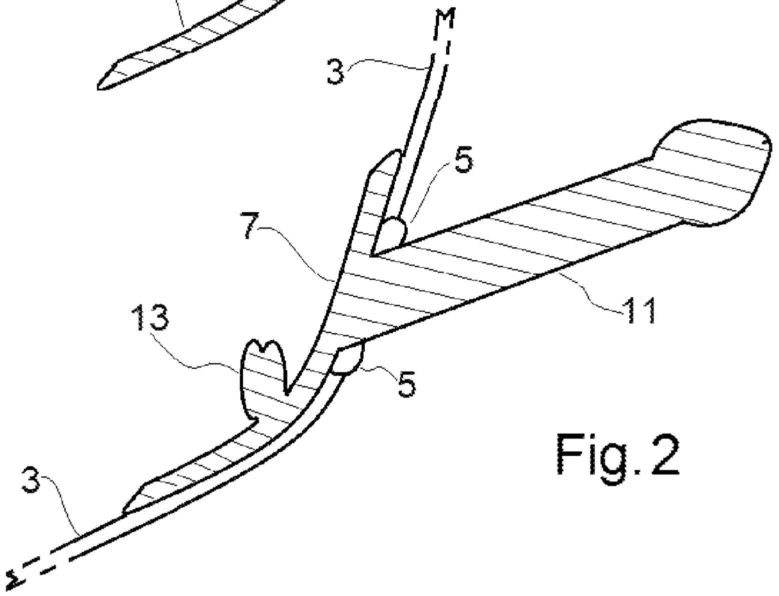
FIG. 2 is a side view of pants with a platform assembly with dildo & rabbit.

FIG. 2, another embodiment of the invention, is a side view of pants 3 with a platform assembly 7 with dildo 11 & rabbit 13. Pants 3 are depicted in FIG. 2 with a rounded opening 5 therein to accommodate dildo 11 as shown.

Figure 3:
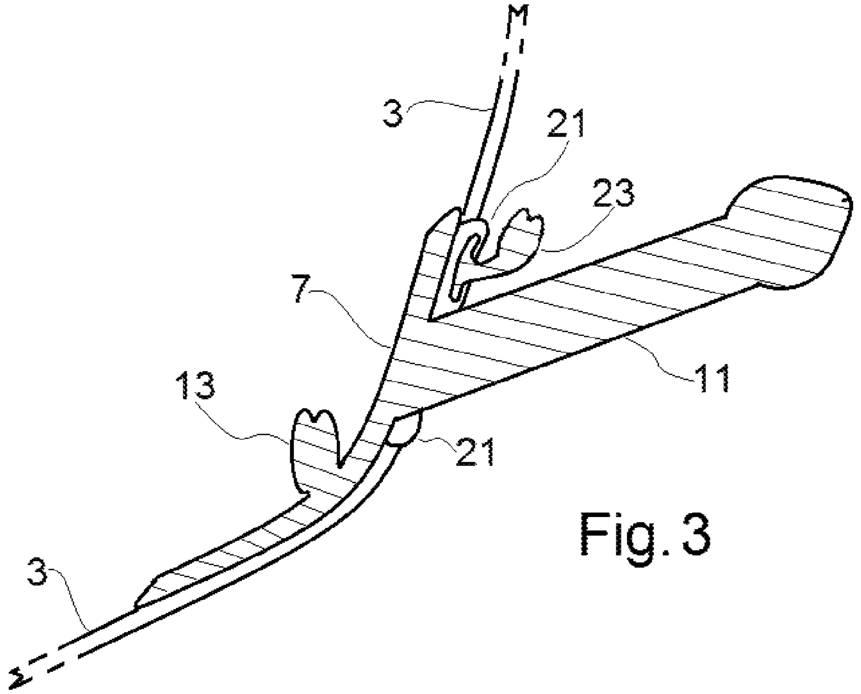
FIG. 3 is a side view of pants with a platform assembly with a dildo & two rabbits.

FIG. 3, another embodiment of the invention, is a side view of pants 3 with a platform assembly 7 with dildo 11 & two rabbits 13 and 23. Pants 3 are depicted in FIG. 3 with a somewhat oval opening 21 therein adapted to accommodate rabbit 23 as shown as well as dildo 11. Rabbits 13 and 23 and dildo 11 illustrated in FIG. 3 may be fix-mounted to, such as being an integral part of, the platform assembly 7, or they may be adjustably mounted as described herein. Rabbit 23 is intended to pleasure the bangee, while rabbit 13 is meant to pleasure the banger.

Figure 4:
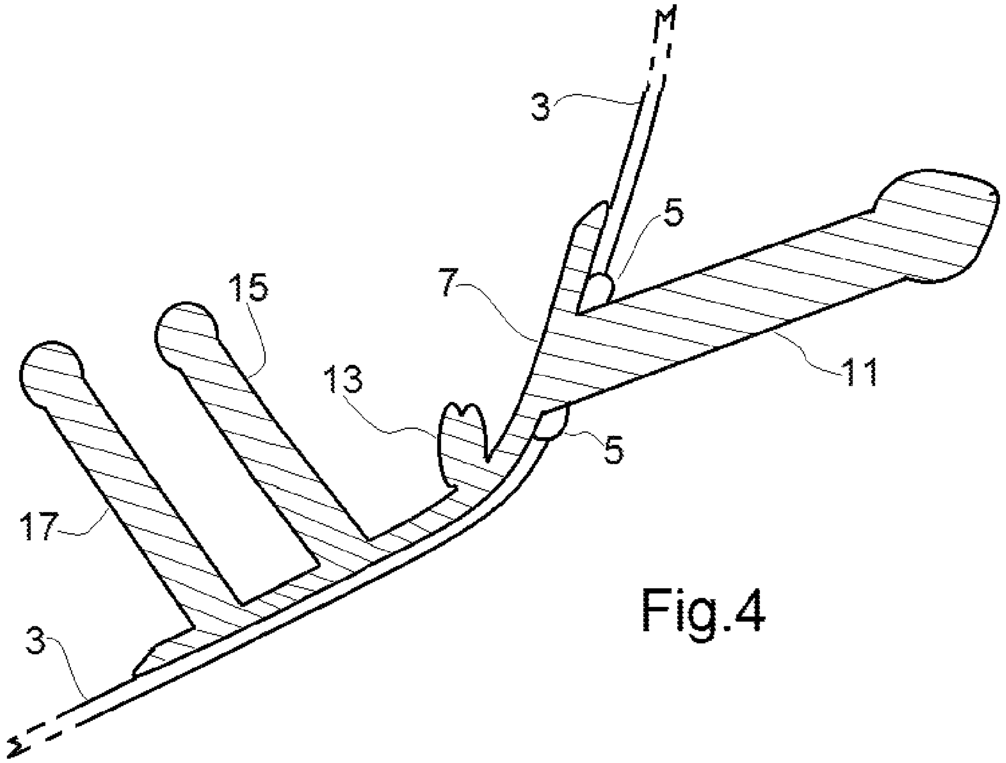
FIG. 4 is a side view of pants with a platform assembly with three dildos & a rabbit.

FIG. 4, another embodiment of the invention, is a side view of pants 3 with a platform assembly 7 with dildos 11, 15 and 17 and rabbit 13. Pants 3 are depicted in FIG. 4 with a rounded opening 5 therein to accommodate dildo 11. When platform assembly 7 of FIG. 4 is worn in pants 3, or in a strap-on harness, dildo 11 sticks out for inserting into a partner while dildo 15 may be inserted in the wearer's vagina and dildo 17 inserted into her anus while rabbit 13 pleasures her clitoris. As mentioned above, dildos, e.g., in FIG. 4, are not, of course, drawn to scale and their depictions in angles shown are not limiting.

The embodiments shown, for example, in FIGS. 1, 2 and 4, may be adapted for a lady to masturbate with; as such, they may be used with or without a holder.

Figure 5:
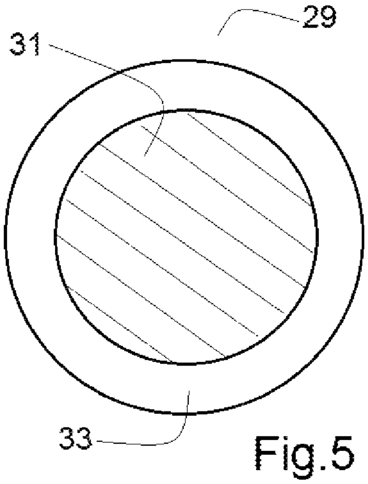
FIG. 5 is a front view of a rounded (crotch) opening in the pants.

FIG. 5, another embodiment of the invention, is a front view of a rounded crotch opening 29 for pants. Opening 31 for a dildo is shown with hatching (a dildo is not shown). Surrounding material 33 of the pants around the opening 31 may have a welt edge with material such as fabric, leather, flexible cord, plastic, rubber, silicone, etc. stitched, glued, pressed or other wise secured, fastened or attached in place around the opening 31. Alternatively, a rigid welt edge, for example, with a ring, such as an o-ring or oval shaped ring, made of plastic, metal, wood, rubber, etc., shaped to fit in surrounding material 33, may be used. Openings for dildos, according to the inventions, would be made in different sizes to fit different dildos.

Figure 6:
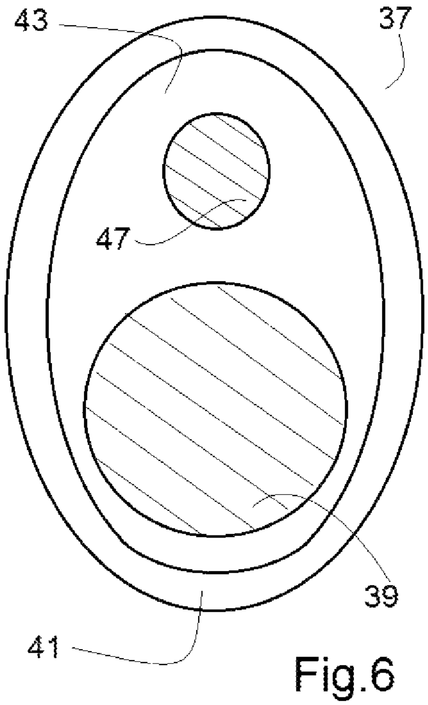
FIG. 6 is a front view of a somewhat oval opening in the pants.

FIG. 6, another embodiment of the invention, is a front view of a somewhat oval crotch opening 37 for pants. Surrounding material 41 of the pants around the somewhat oval crotch opening 37 may have a suitable welt edge similar to that described for FIG. 5. A front view of a portion of a platform assembly 43 is visible through the somewhat oval crotch opening 37; the base 39 of a dildo (not shown) is shown with hatching. The rabbit base 47 for a rabbit (not shown) is also shown with hatching. Rabbit 23 shown in FIG. 3 may be located on rabbit base 47 shown in FIG. 6.

Figure 7:
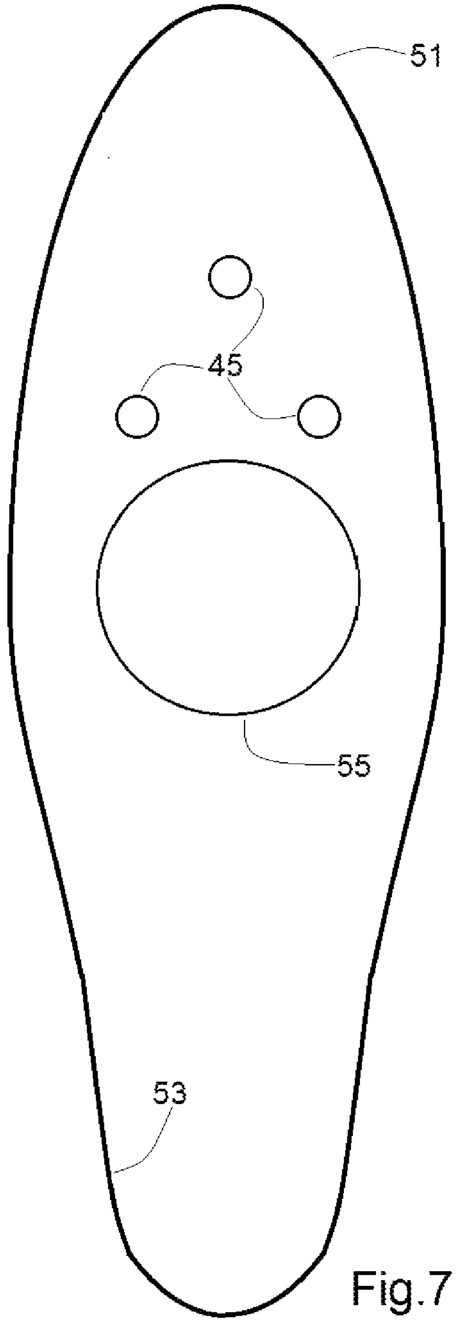
FIG. 7 is a front view of the platform assembly.

FIG. 7, another embodiment of the invention, is a front view of a platform assembly 51. The shape of platform assembly 51 is shown by way of example and not meant to be limiting. As depicted, lower portion 53 may be narrower than the upper portion; this may allow the user a more comfortable and intimate feel and control. The base 55 for a dildo (not shown) is illustrated.

The platform assembly 7 of FIG. 1, for example, may have a lower portion 9 that is narrower than the upper portion, similar to platform assembly 51 in FIG. 7 with a narrower lower portion 53.

Platform Assembly Stiffness:

Platform assembly 7 in, for example, FIG. 1, and platform assembly 51 in FIG. 7, may be flexible and soft, for example, for functional and comfort purposes, or they may be somewhat rigid, for example, to facilitate masturbation embodiments discussed below. Or platform assemblies may be provided with different stiffnesses in different areas of the assembly; for example, a platform assembly may be made more rigid, or more flexible, in the area between the dildo 11 and the rabbit 13, in contrast, for example, to the area(s) above dildo 11 and/or below the rabbit 13.

In FIG. 7 three snaps 45 are illustrated which would allow a rabbit with corresponding snap parts to be snap mounted to platform assembly 51 to please the bangee. For example, rabbit 23, shown in FIG. 3, which may be snapped in place on platform assembly 51 shown in FIG. 7, may be located on rabbit base 47 shown in FIG. 6.

Fastening means other than snaps 45 may be used. For example, any variety of snaps, Velcro, pins, key & slots, dovetail key etc. could be utilized instead of snaps 45 to fasten a rabbit to a platform assembly. Such fastening means may also be used to fasten a dildo to a platform assembly.

If some fastening means, well known in the art, for example, if Velcro (not shown) were used, it could be adapted to allow a rabbit to be adjustably mounted to please a banger's clitoris—located a distance from a dildo so that a lady may position the rabbit in relation to the dildo to accommodate her particular measurements, namely, to position the rabbit to meet her (the banger's) clitoris most comfortably while the dildo is also positioned comfortably for her to bang with. Also, some fastening means could be adapted to allow a dildo to be adjustably mounted instead of or in addition to a rabbit being adjustably mounted. Comfortably locating an inside rabbit in relation to the outside dildo is important for enjoyment.

Figure 8:
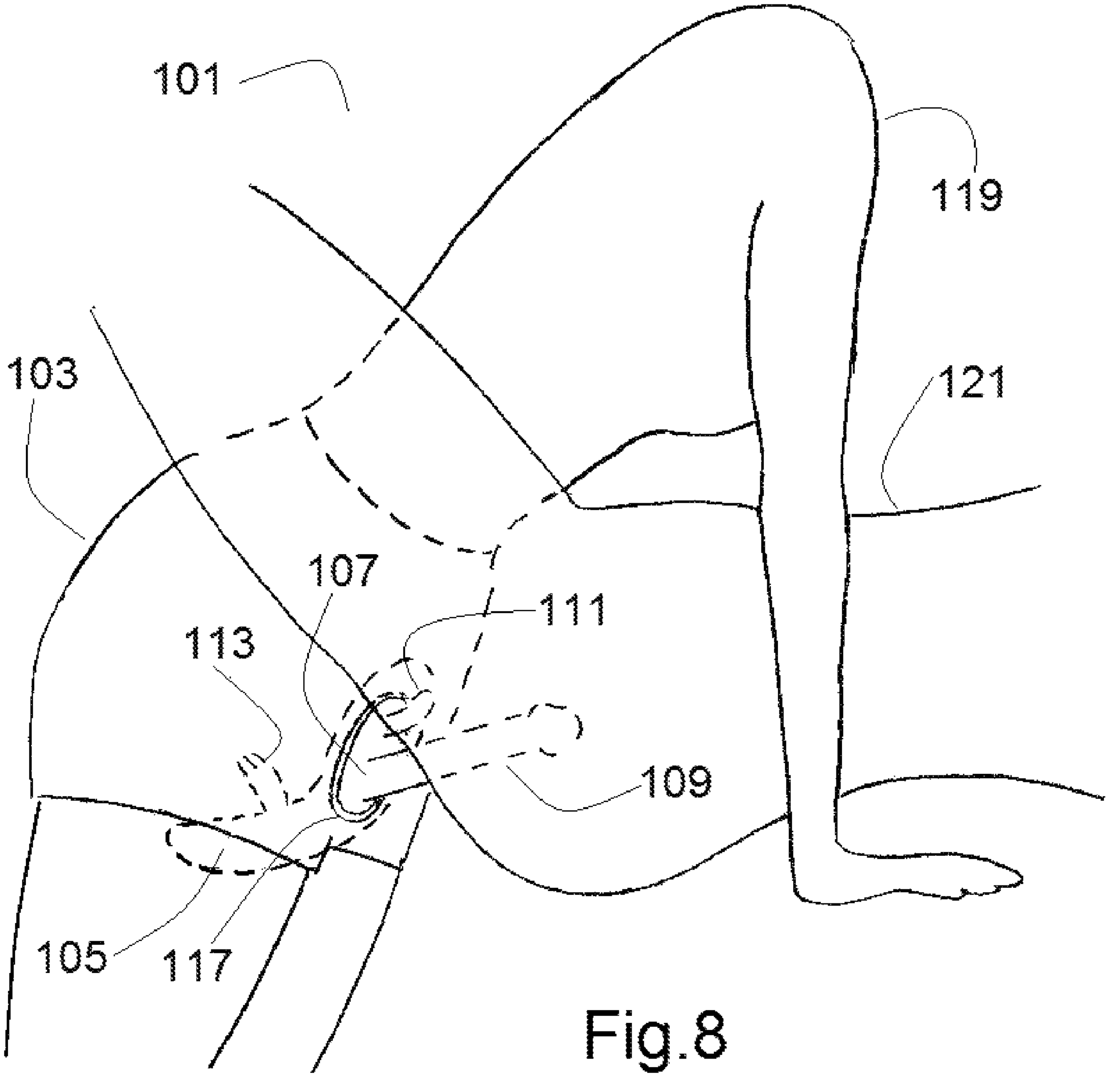
FIG. 8 is a quasi-side oblique see-through view of a lesbian couple banging.

FIG. 8 is a quasi-side oblique see-through view of a lesbian couple 101 banging. A lady user 119, the banger, is illustrated wearing pants 103 with platform assembly 107 inside her pants 103. Lower portion 105 of the platform assembly 107 is illustrated between her legs aimed toward her taint. Rabbit 113 is for her clit's pleasure while rabbit 111 and dildo 109 are for the pleasure of her partner 121, the bangee. As depicted, rabbit 111 and dildo 109, which are part of platform assembly 107, stick out through the somewhat oval opening 117 of pants 103.

Figure 9:
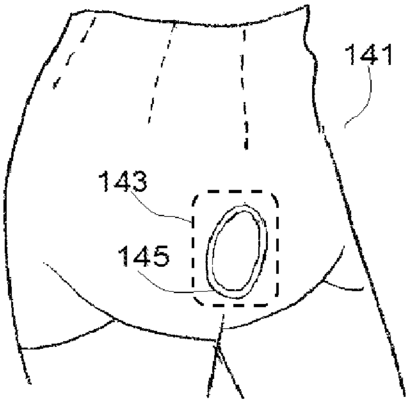
FIG. 9 is a view of pants with an oval opening and the outline of a flap to cover the opening.

FIG. 9, another embodiment of the invention, is a view of pants 141 with a somewhat oval opening 145. Pants 141 are shown to rise high toward the waist to allow a good fit to better hold and control a platform assembly than would pants that fit lower on the hips. Opening 145 may have an associated covering such as a flap that may be located generally as depicted by flap outline 143 to cover oval opening 145. Flap outline 143 also depicts an example of a flap 143 that may be configured with a zipper(s), buttons, Velcro, etc., to be opened or closed and/or to be removable. According to the inventions, other pants described or depicted may have a flap located similar to flap outline 143 to cover an opening according to the inventions.

Figure 10:
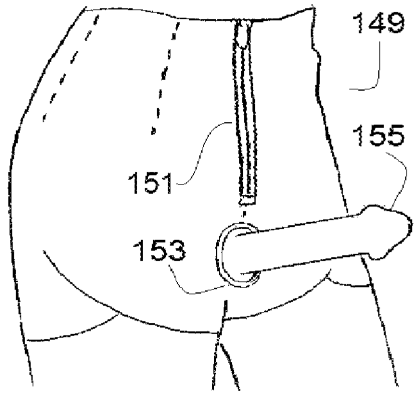
FIG. 10 is a view of pants with a fly and dildo.

FIG. 10, another embodiment of the invention, is a view of pants 149 with a dildo 155 sticking through rounded opening 153. Pants 149 are also shown to fit well in order to better hold and control a platform assembly. Pants 149 are shown with fly 151 (a fly is an opening in or above the crotch area generally as depicted in FIG. 10). The fly 151 may be opened and closed with a zipper, buttons, etc., for example, for dressing or undressing, or for putting in or removing a platform assembly from, pants 149. According to the inventions, other pants described or depicted may have a fly similar to fly 151.

Figure 11:
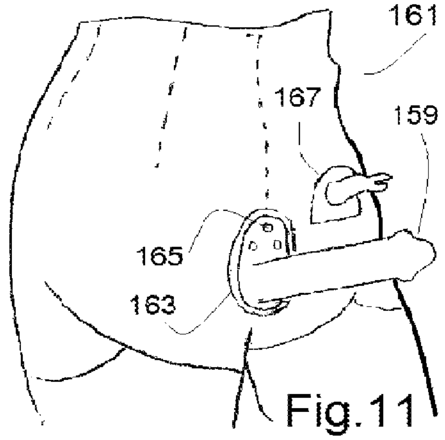
FIG. 11 is a view of pants with a somewhat oval opening with a dildo & detachable rabbit.

FIG. 11, another embodiment of the invention, is a view of pants 161 with somewhat oval opening 163 with dildo 159 shown sticking through somewhat oval opening 163. Detachable rabbit 167 to please the bangee, adapted to be attached to snaps 165, is also shown. Detachable rabbit 167 is shown unattached.

Figure 12:
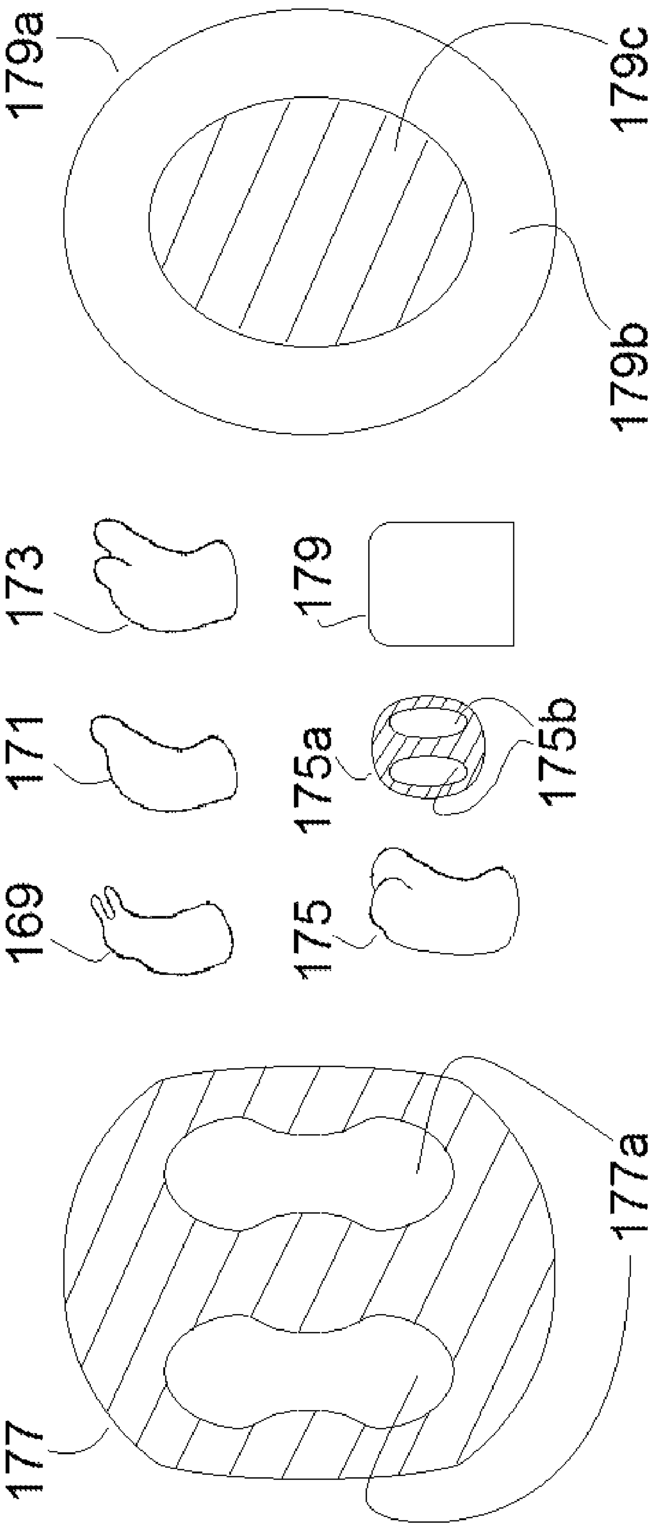
FIG. 12 are depicts various views of different rabbit heads and tops of rabbits.

FIG. 12, embodiments of the rabbit head part of the inventions, are quasi-side views and top views of different shaped rabbits (rabbit heads). For example, rabbit 169 illustrates two tiny fingers or bunny ears, rabbit 171 has a porpoise-nose shape at the top and rabbit 173 illustrates a double porpoise-nose rabbit top. Rabbit 175 is illustrated with two elongated oval shapes 175*b* at the top of rabbit 175 to make contact with or embrace a clitoris. Rabbit top 175*a* is a top view of rabbit 175; the hatched area depicts the body of rabbit 175 seen from the top.

Rabbit 177 is an alternate top view of rabbit 175; the hatched area depicts the body of rabbit 175 seen from the top, and pinched elongated oval shapes 177*a* are a top view of rabbit 175's head, or top, designed to embrace a clitoris comfortably, lovingly and more completely.

Rabbit 179 is a side view of a generally cylindrical shaped rabbit (like a tiny beverage can); top view 179*a* of rabbit 179 depicts a rabbit top 179*b*: Rabbit top 179*b* is configured generally like a doughnut shape which may surround or encompass a clitoris in the recess 179*c*; the doughnut rabbit top 179*b* configuration is depicted to represent a rounded circular shape or oval shape or egg shape doughnut configuration rabbit top. The general diameter dimension of generally cylindrical rabbit 179 may be about 2.5 centimeters give or take a centimeter or so, and the depth of recess 179*c*, depicted with hatching, of rabbit top 179*b* may be about 1 centimeters or so.

Rabbit 13, as depicted in FIGS. 1, 2, 3 and 4, is depicted to be generally shaped like rabbit 177 in FIG. 12. Rabbit head 13 in FIGS. 1, 2, 3 and 4 is depicted off-perpendicular (facing up) relative to platform assembly 7, or alternatively, rabbit head 13 may but more perpendicular, perpendicular or off-perpendicular the other way (facing down) relative to platform assembly 7.

Rabbit 13 in FIG. 1 and rabbit 179 depicted in FIG. 12 and other rabbits herein may be similar in dimensions; for example, rabbits may extend above from a platform assembly anywhere from 1 centimeter or so to about 3 centimeters or so tall (3 centimeters plus/minus high from the platform assembly). By extending above the platform assembly a suitable distance, a rabbit head (top) may enter a banger's genital area somewhat past the labia to contact or embrace the clitoris while the body of the rabbit stimulates other areas of the vulva. By way of example, if cylindrical rabbit 179 were about 3 centimeters tall from the platform assembly, rabbit 179's doughnut configuration rabbit top 179*b*'s hatched recess 179*c* may be about 1 centimeter deep from the high point of doughnut rabbit top 179*b* so that rabbit top 179*b* may contact and encompass a banger's clitoris in recess 179*c*.

Embodiments of the inventions, such rabbit heads, are suitable to be part of, fix mounted, adjustably mounted or detachably mounted to a platform assembly as described herein. For example, a platform assembly with a rabbit to please a banger and a dildo to please a bangee may be moulded in one piece or cut from one piece from any suitable human-safe material, from ubiquitous silicone to rare ivory.

Figure 13:
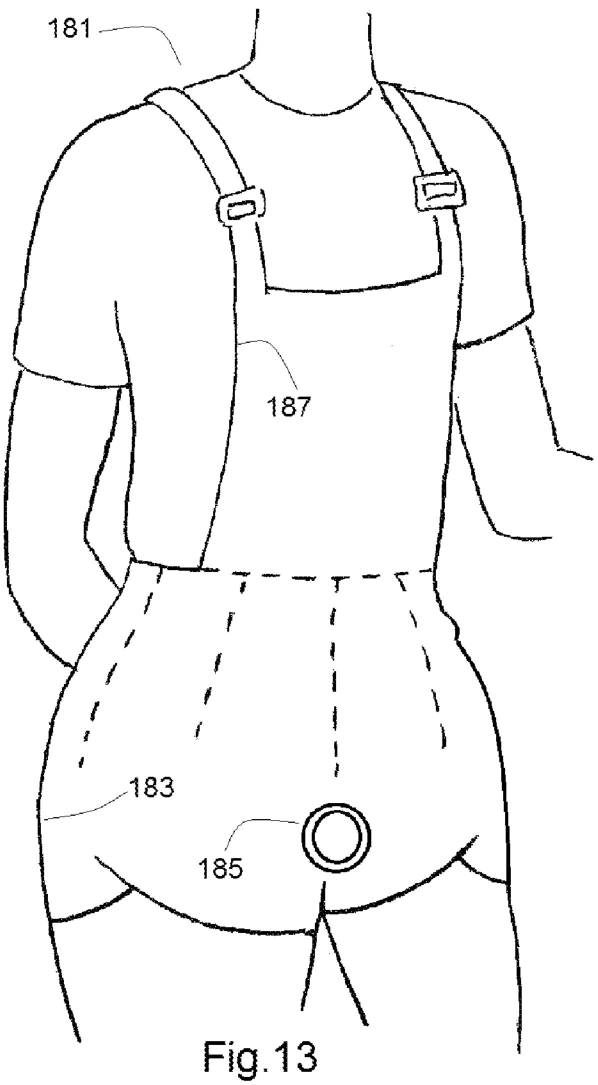
FIG. 13 is a view of pants with a bib and crotch opening.

FIG. 13, another embodiment of the invention, is a view of a banger person 181 wearing bibbed pants 183 with bib 187 and rounded opening 185. Pants 183 may have a somewhat oval shaped opening instead of a rounded opening in accord with embodiments of this invention. The bib 187 may be preferred for a stylish look or, with its adjustable straps, to help hold the pants in place.

Figure 14:
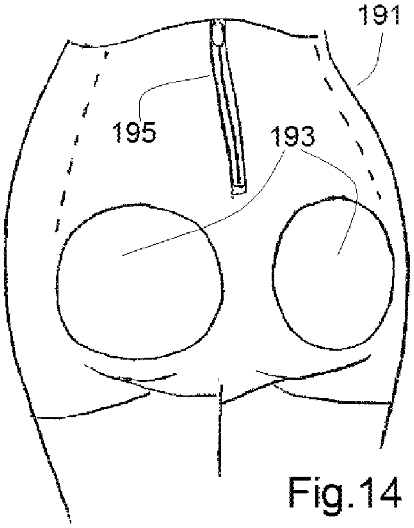
FIG. 14 is a rear view of pants with cheek openings (i.e., butt "cheeks").

FIG. 14, another embodiment of the invention, is a rear view of pants 191 with cheek openings 193 and closure 195. Closure 195 may be on a side, in back as shown in FIG. 14, or in front, like a fly. Closures may be configured with snaps, lacing, zippers, buttons, Velcro etc. The cheek openings 193 allow for the bangee to spank or caress the cheek skin of the banger directly. For example, spanking may increase the banger's and/or bangee's pleasure. Cheek openings 193 will also allow spanked cheeks to show some color, e.g., redness, from spanking, thus perhaps bringing sexual pleasure.

Figure 15:
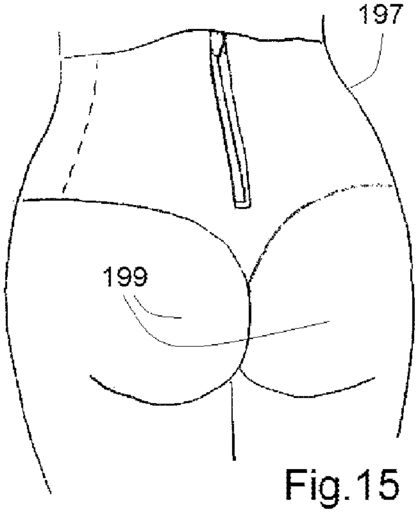
FIG. 15 is a rear view of spanking pants cut high showing the cheeks in the back.

FIG. 15, another embodiment of the invention, is a rear view of pants 197 cut so that the banger's cheeks 199 are exposed for spanking or caressing by the bangee, or for viewing to arouse sexual appetite. The pants 191 and 197 in FIGS. 14 and 15 have a rounded opening or somewhat oval shaped opening in the crotch area on their front in accord with embodiments of the inventions disclosed herein.

Figure 16:
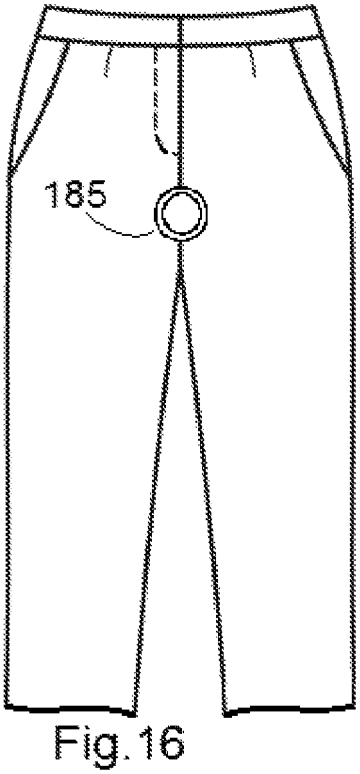
FIG. 16 is a view of long pants with a crotch opening.

FIG. 16, another embodiment of the invention, is a view of long pants with a crotch opening.

Figure 17:
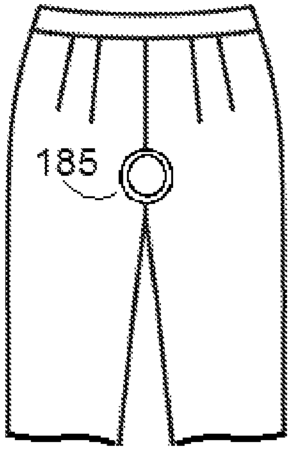
FIG. 17 is a view of capri-type pants with a crotch opening.

FIG. 17, another embodiment of the invention, is a view of capri-type pants with a crotch opening.

Figure 18:
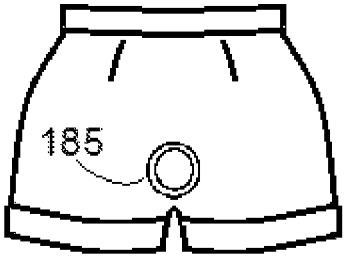
FIG. 18 is a view of short pants with a crotch opening.

FIG. 18, another embodiment of the invention, is a view of short pants with a crotch opening.

Figure 19:
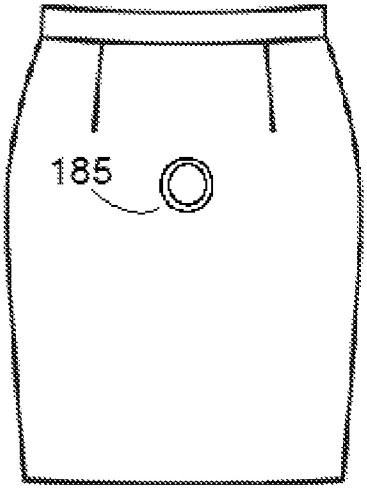
FIG. 19 is a view of a skirt with a crotch opening.

FIG. 19, another embodiment of the invention, is a view of a skirt with a crotch opening.

Figure 20:
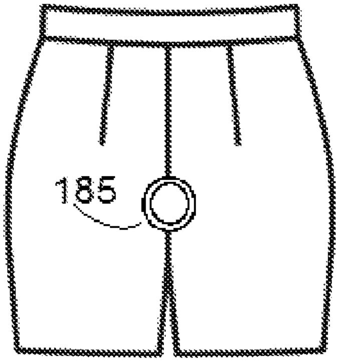
FIG. 20 is a view of short skirt with a crotch opening.

FIG. 20, another embodiment of the invention, is a view of short skirt with a crotch opening.

Figure 21:
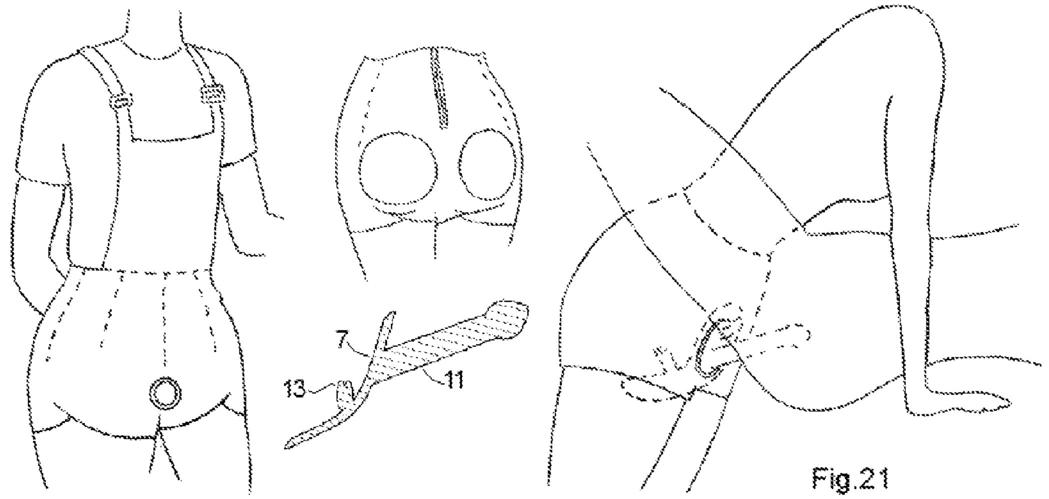
FIG. 21 combines FIGS. 1, 8, 13 and 14 for possible use on the patent face page.

FIG. 21 combines FIGS. 1, 8, 13 and 14 for possible use on the patent face page. FIG. 21 was suggested in the ADS form " . . . for Publication (if any)." FIG. 21 illustrates various embodiments comprising platform assembly 7 with dildo 11 and rabbit 13.

The embodiment shown in FIG. 1 is a side view of a platform assembly with dildo 11 & rabbit 13. The lower portion 9 of platform assembly 7 is designed to extend below a lady user's clitoris while holding the rabbit 13 in contact with her clitoris. The lower portion 9 of platform assembly 7 as illustrated by way of example extends further, past her clitoris toward her taint to cover (envelop or veil) at least part of her vagina or past her vagina to cover at least part of her taint. The lower portion 9 of platform assembly 7 may allow a more intimate feel and control of the dildo, especially if worn in pants; the lower portion 9 may afford a more realistic sensation of having a real penis while banging.

Butt cheek openings, for example as disclosed herein, may be adapted to any hole clothing, for example, FIGS. 13, 16 to 20, 22 and 23.

Figure 22:
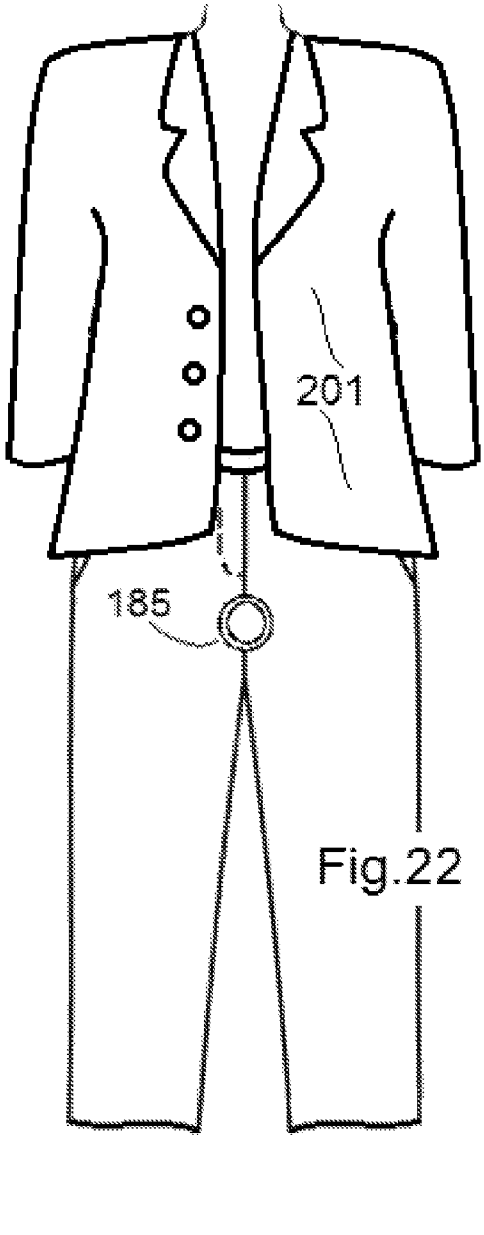
FIG. 22 shows a pant suit with a short jacket and a crotch hole in the pants.
Figure 23:
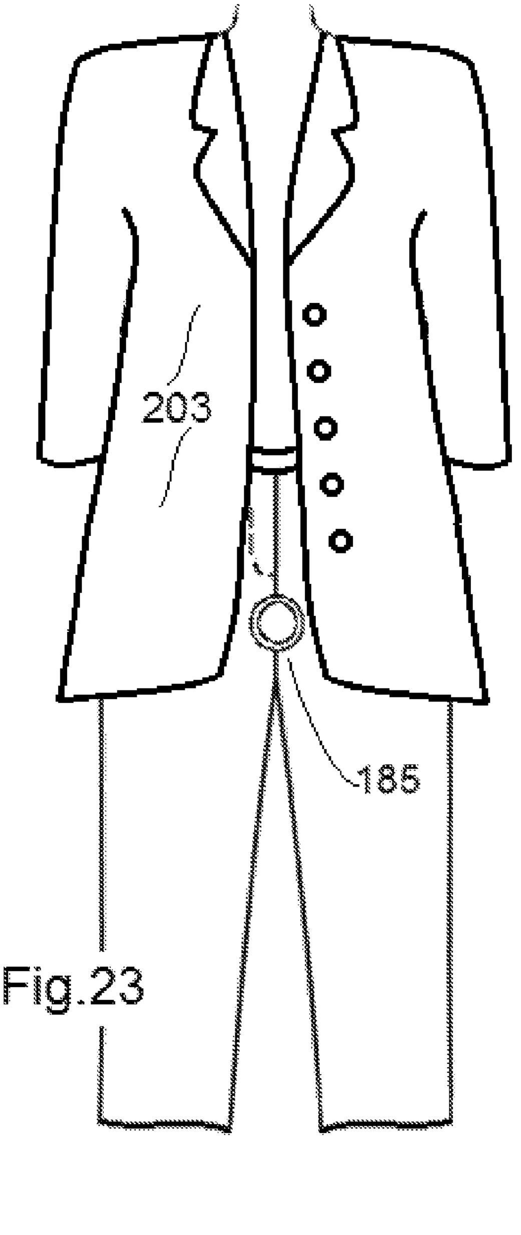
FIG. 23 shows a pant suit with a long jacket and a crotch hole in the pants.

FIGS. 22 & 23 show pant suit combinations with a jacket 201 and 203 respectively suitable for wearing with hole pants. The pants have a rounded crotch hole opening 185 as shown in the pants. The hole pants and the hole pants jacket 201 and 203 may have cheek openings or cheek cutouts or accommodations for spanking purposes. Jackets 201 and 203 may have buttons to button-up the jacket which are orientated traditionally on one side or the other for females or for males; for example, a lady may want to enhance her feelings of maleness by wearing a man's avant-garde jacket in public, or while banging a sex partner.

The pants embodiments of the inventions may be worn ostensibly to hold a platform assembly. The pants as disclosed herein may be worn with or without using a platform assembly; they may be worn at times because they appear attractive or sexy to some users of the inventions, or they may be worn by others who may prefer not to use the platform assemblies; for example, various pants disclosed for the inventions may be worn in public. That might be considered unusual, but that way, people, males and females, could, for example, without using the platform assembly, advertise their interest in interesting sex play for friends and strangers alike to see. The visible empty opening in the crotch area of the pants would not only alert other savvy people, but it would no doubt, also be the subject of questions (from males and females) like, what's the hole for? An unusual conversation starter, pants may be suitable only where appropriate; for example, for some sophisticated seminars, motivational talks, cocktail & office parties and other adult gatherings. Perhaps college people are old enough and would also like to wear new "hole pants" and maybe even utilize a platform assembly if they are in a safe loving relationship.

Flap 143 depicted in pants 141 of FIG. 9 may be used to cover the opening when it may be inappropriate for the wearer to show the opening, for example, when traveling on public transportation. The wearer may select preferred panties for wearing with pants since the panties will show through the opening when not covered by a flap.

There is a broad market for the pants clothing, for example, as shown in the figures and described herein—for example: sexually "straight" people who are into avant-garde fashion, or people who want to make a "politically correct" statement, or people who merely sympathize or support the LGBT community, "Lesbian, Gay, Bisexual & Transgender."

In accord with the inventions, long pants, short pants, any pants and any skirts may be provided with rounded or somewhat oval shaped crotch openings, as well as cheek openings for spanking or viewing as depicted in, for example, FIGS. 14 and 15. The pants embodiment depicted in FIG. 13, for example, may also expose a banger's cheeks as depicted, for example, in FIGS. 14 and 15.

In practice, comfort is important, for example, in regard to the location of the rabbit on the platform assembly inside the pants to the dildo sticking outside. When the rabbit is comfortably located on the pants wearer's clitoris, the location of the dildo to be used by the banger for banging a partner is also important for her comfort, pleasure and control, and ultimately, for the bangee's comfort and pleasure as well.

In accord with the inventions, a variety of platform assemblies may be made available. Different platform assemblies will have, for example, different numbers of rabbits and dildos, rabbits and dildos that are attached in different ways to the platform assembly, the inside rabbit at different distances from an outside dildo(s), different sizes of rabbits and dildos, with and without vibrator(s), different colors etc. In accord with the inventions, a variety of pants may be made available and the openings they may vary in size, shape and location (such as higher or lower) on the pants.

Ordering Considerations for Platform Assemblies and Pants

For a given platform assembly, the position of the opening in the pants determines the location of the rabbit in relation to the banger's clitoris as well as the location of the outside dildo. When purchasing a platform assembly and pants according to the inventions, a person would preferably consider the anatomy of the intended banger. The bangee may prefer to specify the size, girth and length, of the dildo. One approach is for the intended banger to first select, for example, a given platform assembly with a distance she desires between the inside rabbit and outside dildo, and then select the pants that has the opening positioned to locate the platform assembly (which is controlled by the dildo sticking out through the opening) accordingly. Such ordering considerations include:

Clitoris Location Measurement for Ordering a Platform Assembly:

A variety of platform assemblies, such as those shown by way of example in FIGS. 1, 1A, 2, 3, 4 and 8, may be offered. Other assemblies, for example, such a one having two outside dildos (not shown) are possible if a lady bangee wants both vaginal and anal banging pleasure from her banger.

Considerations for ordering a platform assembly as depicted in FIG. 1, by way of example, with an inside rabbit and outside dildo: For a given pair of pants, or an adjustable strap-on dildo harness, assume the given platform assembly's rabbit is comfortably located for the intended banger's clitoris. The distance between the platform assembly's rabbit and dildo should be considered, measured and selected to afford the banger pleasure of a comfortably located rabbit for her clitoris and a realistic sensation of having a real penis while banging. For example, what is the measurement between the intended banger's clitoris and the central area of the pubic symphysis? Having the dildo positioned on the pubic symphysis may allow optimum realistic thrusting (banging). To achieve such comfort, when offering platform assemblies, a provider may ask a potential customer to provide an indication of her measurements, and provide instructions how to measure between her clitoris and where she wants the center of the base of the dildo to be.

The platform assembly 7 of FIG. 1, for example, may have a lower portion 9 that is narrower than the upper portion, similar to platform assembly 51 in FIG. 7 with a narrower lower portion 53.

Also, a provider may give instructions to a potential customer regarding selecting the shape of the rabbit head and the dimension of the rabbit. For example, for an average female person, rabbit 13 with pinched elongated FIG. 12's oval shapes 177*a,* 2 centimeters to the top of 177*a* measured from the platform assembly, might be a popular choice because of its comfort, feel and effectiveness. Or, rabbit 179 with its doughnut shaped top to encompass a clitoris may be an even more popular choice.

Clitoris Location Measurement for Ordering Pants:

Bear in mind that the location of the intended banger's clitoris has already been taken into account in relation to the dildo when the platform assembly was selected.

To provide pants with the opening comfortably located for an already selected platform assembly, when offering pants according to the inventions, a provider may ask a potential customer, where is the intended wearer's clitoris located? Is it high up toward the belly button, average, or lower than average? Three selections may be offered: 1) high up, 2) average, and 3) lower than average (closer to the anus). Or the provider may ask a customer to provide the measurement, and provide instructions on how to take that measurement, such as how to locate the pubic symphysis area from which to measure the distance to the clitoris. If a platform assembly is intended to be used with a strap-on harness which allows adjustment of the harness's opening which accommodates a dildo, the above clitoris location measurement concerns for ordering pants may be avoided.

In other words, selecting the appropriate distance between the rabbit and dildo in FIG. 1's platform assembly ensures comfortable rabbit positioning for the banger's clitoris as well as an intimate feel and control of the dildo for a more realistic sensation of having a real penis, and the location of the hole in the pants determines if the platform assembly will be positioned in accord with the location the banger wants her rabbit and faux penis positioned. It is nice to have a faux penis; clitoral stimulation is nicer.

To achieve preferred usage and pleasure from a chosen platform assembly, these ordering considerations above are important, and, also important, are properly fitting, for example, tight fitting, high waisted pants in order to offer the best comfort from the rabbit for the banger's clitoris as well as give the banger the best control and use of the dildo for her and her partner's pleasure. Pants may also have a low waist, or another type, if the banger prefers. A proper fitting pair of pants that tightly hold the rabbit and dildo in place will allow improved banging for both the banger and bangee.

In another embodiment of the invention, a supplier's Internet webpage store, for example, selling various Rabbutt products, may offer one or more printable cutout(s) to aid in selecting the best platform assembly and Pants to fit a particular customer's body. The cutout might be generally shaped, for example, like the platform assembly 51 with narrow lower portion 53 as shown in FIG. 7. The seller's webpage instructions might suggest, for example, to print and cut out the shape that seems most suitable for the comfort and satisfaction of her body, hold it in place between her legs and mark with a marker, for example, "A" for her anus, "V" for her vagina, "C" for her clitoris and "P" for where she would like the center of the base of the dildo to be located. A marked-up cutout could be scanned and sent to the supplier via email or USPS, for example, with an order.

An order may (also) contain, for example, the customer's wishes for dimensions, shapes, etc., such as the length and girth of the dildo, shape/size of the rabbit, etc.

A supplier could offer custom built products or off-the-shelf products that fit, for example, the markings on the cutout and/or dimensions of the dildo. Such marking could, for example, be detected electronically by supplier software developed to match an off-the-shelf product, or software may produce a product made to customer specifications.

Masturbation:

Embodiments of the invention can also be enjoyed by a lone lady for a masturbating experience, including, for example, a unique combination of sexual sensations. While wearing the platform assembly in pants or a strap on harness with the dildo portion sticking through the opening and the rabbit engaging her clitoris, the wearer can use the dildo to manipulate the rabbit to maximize the stimulation of her clitoris. In this manner, a whole new sexual sensation can be achieved—a lady pleasuring her clitoris with a rabbit while using a phallic device to control the rabbit. A platform assembly may even be used for masturbation without pants or a harness; a lady can hold the platform assembly in place with the dildo while pleasuring her clitoris.

Such embodiments may appeal to a lady who fancies her clitoris and also having a penis. For example, it could be likened to masturbating a clitoris & masturbating a penis simultaneously. Indeed, for some, it may become the preferred or the only way to masturbate when no one else is around to enjoy sex with, or to maintain celibacy for moral, religious or other reasons.

This single use pleasure sensation embodiment (e.g., masturbation, self-stimulation) with or without a holder, as well as other embodiments, can be enhanced (adapted for use with), for example, with one or more of the following: vibrator technology, squirting dildo technology and mechanized dildo technology and textured dildos; such technologies are well known in the sexual arts These and other stimulation enhancing technologies can be configured with platform assemblies described and illustrated above, including assemblies that have soft or somewhat rigid stiffness, or have areas on the assembly that have differing stiffness.

Endnotes & Caressing

Pants according to the inventions with provisions for spanking are examples of embodiments of the inventions being disclosed. It is also true such provisions allow for more tender caressing. The pants described herein may have closures on a side, in back or in front, and closures may be snaps, lacing, zippers, buttons, Velcro etc. As described herein, pants according to the inventions may have a fly.

Dildo and rabbit components may be adjustably attached to the platform assembly by snaps, lacing, zippers, buttons, Velcro etc., or they may be non-adjustable such as being fix mounted to a platform assembly, such as being an integral part of a one piece molded platform assembly. Or, dildos and rabbits may be affixable to the platform assembly with various substances like different adhesives with different holding properties; this may, for example, afford the banger a more custom fit for the rabbit on her clitoris and feel for the faux penis while banging. Components of embodiments of these inventions may be ordered “off the shelf/rack” or they may be custom ordered.

Certain changes and modifications of the embodiments of the inventions disclosed herein will be readily apparent to those skilled in the arts. It is the Applicant’s intention to cover by the claims all such uses of the inventions and all those changes and modifications which could be made to the embodiments of the inventions herein chosen for the purpose of disclosure without departing from the spirit and scope of the inventions.

These are trademarks that have been selected and used for the inventions sought herein: “Rabbutt™” and “Rabbutt Hole Pants™”

I claim:

1. A sex paraphernalia platform assembly adapted to be worn by a female giver configured with a dildo for giving facing one way on one side of a first assembly and a clitoral stimulator on the other side of the assembly facing the other way to stimulate a female giver’s clitoris while she is giving to another with the dildo, an improvement comprising:

said assembly having a lateral mid area between the dildo on one side and the clitoral stimulator on the other, the stimulator being attached to the platform assembly and spaced a distance from the bottom of the dildo by the lateral mid area, wherein said stimulator provides the giver with improved stimulation while the giver is giving to another.

2. The platform assembly of claim 1 comprising an associated second platform assembly wherein the spaced distance is different than the spaced distance of said first platform assembly.

3. The platform assembly of claim 1 wherein the assembly has a substantial upper area above the dildo.

4. The platform assembly of claim 1 wherein the stimulator is a rabbit.

5. The platform assembly of claim 4 wherein the rabbit generally comprises a cylindrical shape.

6. The platform assembly of claim 5 wherein the rabbit is affixably attached to the platform assembly.

* * * * *